United States Patent [19]

Aufderhaar et al.

[11] 4,205,077
[45] May 27, 1980

[54] BENZIMIDAZOLE SULPHIDES AS ANTHELMINTIC AGENTS

[75] Inventors: Ernst Aufderhaar, Kaiseraugst; Jean J. Gallay, Magden; Manfred Kühne, Pfeffingen; Alfred Meyer, Basel; Oswald Rechsteiner, Binningen; Max Schellenbaum, Muttenz; Jean-Paul Fumeaux, Basel, all of Switzerland

[73] Assignee: Ciba-Geigy Corporation, Ardsley, N.Y.

[21] Appl. No.: 894,974

[22] Filed: Apr. 10, 1978

[30] Foreign Application Priority Data

Apr. 12, 1977 [LU] Luxembourg ............... 77121
Apr. 12, 1977 [LU] Luxembourg ............... 77122
Mar. 14, 1978 [LU] Luxembourg ............... 79227

[51] Int. Cl.$^2$ .............. A61K 31/415; C07D 235/20; C07D 235/28
[52] U.S. Cl. .............. 424/273 B; 548/305; 548/328
[58] Field of Search ............... 548/305, 328; 424/273 R, 273 B

[56] References Cited

U.S. PATENT DOCUMENTS 3,506,767  4/1970  Frick et al. ............... 548/305

*Primary Examiner*—Natalie Trousof
*Attorney, Agent, or Firm*—Frederick H. Rabin

[57] ABSTRACT

Benzimidazole derivatives of the formula

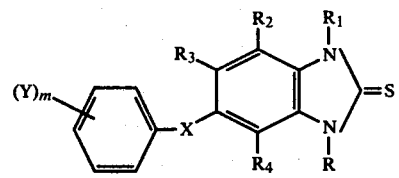

in which R and $R_1$ independently of one another are each hydrogen, an alkanoyl group having 1 to 4 carbon atoms, an alkoxycarbonyl group having 1 to 4 carbon atoms, an alkylsulphonyl group having 1 to 4 carbon atoms, a benzoyl group, a phenylsulphonyl group or a p-methylphenylsulphonyl group; $R_2$ and $R_4$ independently of one another are each hydrogen, halogen or a methyl group, $R_3$ is hydrogen, halogen, a methyl group or a methoxy group; X is oxygen or sulphur; Y is halogen, an alkyl group having 1 to 4 carbon atoms, an alkoxy group having 1 to 4 carbon atoms, a methylthio group, a methylsulphinyl group, a methylsulphonyl group, a trifluoromethyl group, a nitro group, a hydroxyl group, a cyano group or an acetyl group; and m is 0, 1, 2 or 3; and if one of the two radicals R or $R_1$ is hydrogen, the position of the other of these radicals on the N atoms cannot be clearly established, including, when at least one of the two radicals R or $R_1$ is hydrogen, the possible tautomeric compounds of the formula I; and the disulphides obtainable by oxidation of compounds of the formula I. The compounds are useful for combating helminths in domestic animals and productive animals.

8 Claims, No Drawings

BENZIMIDAZOLE SULPHIDES AS ANTHELMINTIC AGENTS

DETAILED DISCLOSURE

The present invention relates to novel benzimidazole derivatives having an anthelmintic activity, processes for the preparation of these compounds, agents containing these compounds as the active ingredient and their use for combating helminths, especially trematodes, in domestic and useful animals.

The compounds according to the invention are of the general formula I

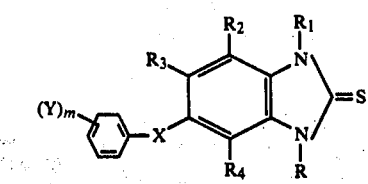

in which R and $R_1$ independently of one another are each hydrogen, an alkanoyl group having 1 to 4 carbon atoms, an alkoxycarbonyl group having 1 to 4 carbon atoms, an alkylsulphonyl group having 1 to 4 carbon atoms, a benzoyl group, a phenylsulphonyl group or a p-methylphenylsulphonyl group; $R_2$ and $R_4$ independently of one another are each hydrogen, halogen or a methyl group; $R_3$ is hydrogen, halogen, a methyl group or a methoxy group; X is oxygen or sulphur; Y is halogen, an alkyl group having 1 to 4 carbon atoms, an alkoxy group having 1 to 4 carbon atoms, a methylthio group, a methylsulphinyl group, a methylsulphonyl group, a trifluoromethyl group, a nitro group, a hydroxyl group, a cyano group or an acetyl group; and m is 0, 1, 2 or 3; and if one of the two radicals R or $R_1$ is hydrogen, the position of the other of these radicals on the N atoms cannot be clearly established, including, when at least one of the two radicals R or $R_1$ is hydrogen, the possible tautomeric compounds of the formula I; and the disulphides obtainable by oxidation of compounds of the formula I.

Halogen, as $R_2$, $R_3$ and $R_4$ in formula I and as Y in formula IV, is to be understood as meaning, preferably, chlorine or bromine.

In the present description, "helminths" are to be understood as meaning parasitic nematodes, cestodes and trematodes in the gastrointestinal tract or in other organs.

Amongst the endoparasites occurring in warm-blooded animals, the helminths in particular cause great damage. Thus, animals infested by these parasites display not only a retarded growth and a distinctly reduced performance but, in some cases, such severe damage that the diseased animals die. In order to prevent or at least lessen losses of returns from this type in animal husbandry, which can assume considerable proportions if cases of infestation with worms in the animal herds are of an epidemic nature, efforts are continually being made to provide agents for combating helminths, including their development stages.

It is true that a number of substances having an anthelmintic activity are known, but these active ingredients are not able to meet the demands made on them in the desired manner since, for example, they do not exhibit an adequate activity in every case when administered in tolerated doses or, when administered in a therapeutically effective dosage, can cause undesired side effects, such as intoxications.

Thus, for example, benzimidazole derivatives are mentioned in British Pat. No. 1,344,548 and in French Pat. No. 1,476,558 for use in various fields, including, in the latter specification, in a general form, the possibility of use against helminths.

It is now proposed to employ the benzimidazole derivatives, according to the invention, of the formula I for combating helminths.

The benzimidazole derivatives of the formula I are distinguished by superior anthelmintic activity, especially against trematodes, and in particular their action against Fasciolidae (for example *Fasciola hepatica*) is to be singled out.

Amongst these derivatives, the compounds which fall under the following restricted formula II are to be regarded as preferred, in respect of their activity:

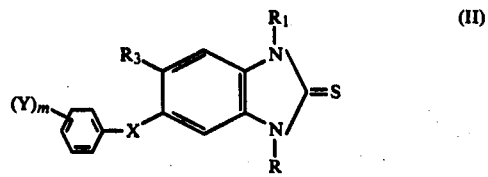

in which R and $R_1$ independently of one another are each hydrogen, an alkanoyl group having 1 to 4 carbon atoms, an alkoxycarbonyl group having 1 to 4 carbon atoms or a benzoyl group; $R_3$ is hydrogen, chlorine or a methyl group; X is oxygen or sulphur; Y is halogen, a methyl group, a methoxy group, a methylthio group, a methylsulphinyl group, a methylsulphonyl group, a nitro group, a hydroxyl group, a cyano group or an acetyl group; and m is 0, 1, 2 or 3; and if one of the two radicals R and $R_1$ is hydrogen, the position of the other of these radicals on the N atoms cannot be clearly established, including, when at least one of the two radicals R and $R_1$ is hydrogen, the possible tautomeric compounds of the formula II; and the disulphides obtainable by oxidation of compounds of the formula II.

Furthermore, compounds of the following restricted formula III are characterised by high activity:

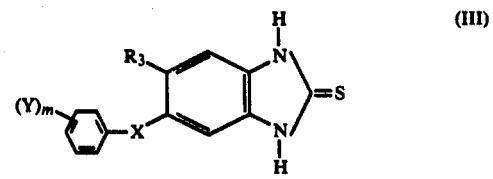

in which $R_3$ is hydrogen, chlorine or a methyl group, X is oxygen or sulphur; Y is halogen, a methyl group, a methoxy group, a methylthio group, a methylsulphonyl group, a cyano group or an acetyl group; and m is 0, 1 or 2; including the possible tautomeric compounds of the formula III and the disulphides obtainable by oxidation of compounds of the formula III.

Moreover, compounds of the following restricted formula IV are distinguished by an advantageous therapeutic activity:

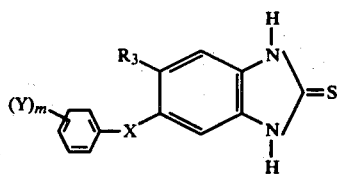

in which $R_3$ is hydrogen, chlorine or a methyl group; Y is halogen or a methyl group, with the proviso that the 2-position of the phenyl radical bonded via an oxygen atom must always be occupied by a substituent as defined for Y and the 6-position of this phenyl radical must always be unoccupied and m is 1 or 2; including the possible tautomeric compounds of the formula IV and the disulphides obtainable by oxidation.

The compounds of the formula I can be prepared by the following processes:

Process I

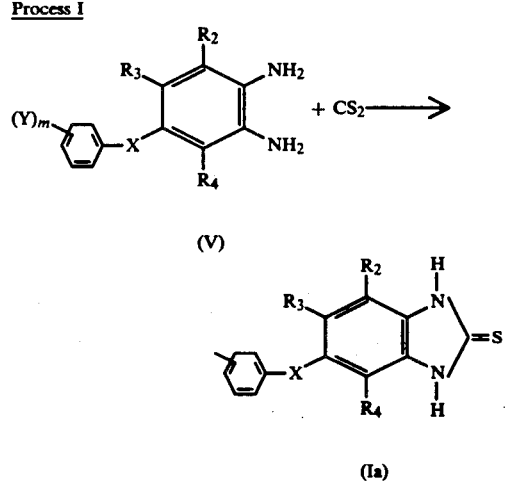

in which formulae $R_2$, $R_3$, $R_4$, X, Y and m are as defined under formula I. The reaction takes place at temperatures of 10° to 150° C., preferably 30° to 100° C., in water or organic solvents, in the presence of a base.

Examples of organic solvents are alcohols, such as methanol, ethanol or the propyl alcohols, or hydrocarbons, such as benzene or toluene, or chlorinated hydrocarbons, such as chlorobenzene or methylene chloride. Bases are to be understood as meaning, for example, an alkali, tertiary amines or organic bases, such as pyridine.

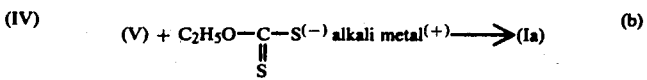

The reaction takes place at temperatures of 20° to 150° C., preferably 50° to 100° C., in water or organic solvents.

Examples of organic solvents are alcohols, such as methanol, ethanol or the propyl alcohols, or hydrocarbons, such as benzene or toluene, or chlorinated hydrocarbons, such as chlorobenzene or methylene chloride.

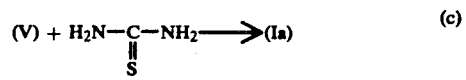

The reaction takes place by melting together the reactants at temperatures of 150° to 220° C., preferably 170° to 190° C. and the starting compound (V) must be in the form of the hydrochloride.

(d)

The reaction takes place at temperatures of 0° to 120° C., preferably 20° to 80° C., in water or organic solvents which are inert towards the reactants.

Examples of inert organic solvents are ethers, such as dioxane or tetrahydrofurane, or hydrocarbons, such as benzene or toluene, or chlorinated hydrocarbons, such as chlorobenzene or chloroform.

(e)

The reaction takes place at temperatures of 60° to 180° C., preferably 80° to 150° C., without a solvent or in the presence of water or alcohols, such as methanol, ethanol or the propyl alcohols, and the starting compound (V) must be in the form of the hydrochloride.

The methods used according to process I for the preparation of the compounds of the formula Ia are known processes which are described in the literature as indicated below:

Process (a): J. Chem. Soc. 1950, 1515–1519
Process (b): Org. Syntheses Coll. Vol. IV, 569–570
Process (c): J. prakt. Chemie 75 (1907) 323–327
Process (d): Chem. Ber. 20 (1887) 228–232
Process (e): Ann. 221, (1883) 1–34 Ann. 228, (1885) 243–247

Process II

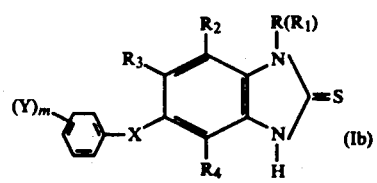

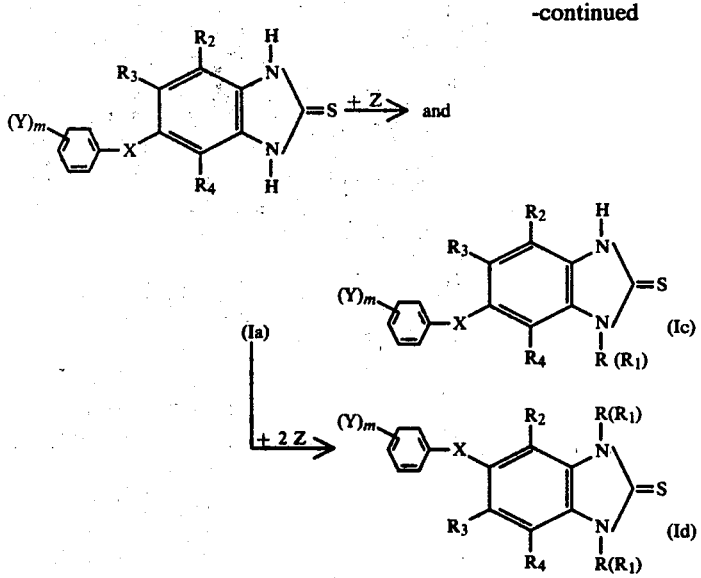

in which formulae R, $R_1$, $R_2$, $R_3$, $R_4$, X, Y and m are as defined under formula I except that R and $R_1$ must not be hydrogen, and Z is as defined specifically in process variants (a) to (c) described below.

(a)

Z=$(R_1)_2O$ or $(R)_2O$, and $R_1$-Hal or R-Hal, in which $R_1$ and R are alkanoyl or benzoyl and Hal is halogen.

The reaction is carried out at temperatures of $-20°$ to $+100°$ C., preferably 0° to 60° C., in inert organic solvents, in the presence of organic or inorganic bases or without bases.

Examples of organic solvents are: ethers, such as dioxane or tetrahydrofurane, hydrocarbons, such as benzene or toluene, and, in addition, dimethylformamide. Bases are to be understood as meaning, for example, pyridine or NaH.

(b)

Z=$R_1$Cl or R-Cl, or $R_1$-ester or R-ester, in which $R_1$ and R are alkylsulphonyl, phenylsulphonyl or p-methylphenylsulphonyl.

The reaction is carried out at temperatures of $-20°$ to $+100°$ C., preferably 0° to 60° C., in inert organic solvents, in the presence of organic or inorganic bases, or without bases.

Examples of organic solvents are: ethers, such as dioxane or tetrahydrofurane, hydrocarbons, such as benzene or toluene, and, in addition, dimethylformamide.

(c)

Z=$R_1$-Hal or R-Hal, in which $R_1$ and R are alkoxycarbonyl and Hal is halogen.

The reaction is carried out at temperatures of $-20°$ to $+100°$ C., preferably 0° to 60° C., in inert organic solvents, in the presence of organic or inorganic bases, or without bases.

Examples of organic solvents are: ethers, such as dioxane or tetrahydrofurane, hydrocarbons, such as benzene or toluene, and, in addition, dimethylformamide. Bases are to be understood as meaning, for example, pyridine or NaH.

The methods used in process II for the preparation of the compounds of the formulae Ib, Ic and Id are known processes which are described in J. Het. Chem. 6 (1969) 23–28.

Process III

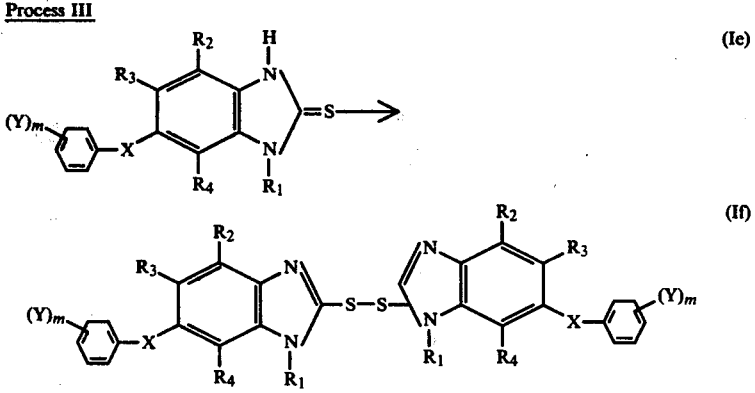

in which formulae $R_1$, $R_2$, $R_3$, $R_4$, X, Y and m are as defined under formula I.

The reaction takes place at temperatures of 0° to 100° C., preferably 10° to 60° C., in water or organic solvents, for example hydrocarbons, alcohols, ketones or dimethylsulphoxide, in the presence of oxidising agents, for example $R_2O_2$ or $I_2$.

The method used according to process III for the preparation of the compounds of the formula If comprises known processes which are described in the literature as indicated below: J. Chem. Soc. 1930, 2402–2408, Bull. Chem. Soc. Japan 49, 1441–1442, Japanese Patent Specification No. 28,499/69 and Arch. Pharm. 291, 180–184 (1958).

Some of the starting compounds used for the preparation of the compounds, according to the invention, of the formula I are known. Thus, for example, some of the compounds of the formula V are described in Swiss Patent Specification No. 462,847. The starting compounds can be prepared by known processes.

Preparation of
5-chloro-6-(2',4'-dichlorophenoxy)-2H-1,3-dihydro-benzimidazole-2-thione

EXAMPLE 1

256.2 g of 4-chloro-5-(2',4'-dichlorophenoxy)-1,2-phenylenediamine are added to a solution of 135.6 g of potassium hydroxide in 540 ml of absolute ethanol. 480.2 g of carbon disulphide are then added dropwise to the mixture in the course of half an hour with stirring, at room temperature, without external cooling. The reaction is slightly exothermic. During the second quarter of the addition, a brown precipitate separates out. The mixture is subsequently heated to the reflux temperature and kept at a bath temperature of 60° C. for 6 hours and then stirred at room temperature for a further 15 hours. The suspension is poured into 6 l of ice-water and the precipitate is filtered off, washed with about 3 l of water and dried in vacuo at 50° C. The crude product is dissolved in 10 l of hot acetone, the solution is clarified with active charcoal and filtered through Hyflosupercel and the filtrate is concentrated to 4 l and then cooled to 0°. The precipitate which has formed is filtered off, washed with acetone and dried in vacuo at 40°. This gives 266 g of 5-chloro-6-(2',4'-dichlorophenoxy)-2H-1,3-dihydro-benzimidazole-2-thione with a melting point of 309°–311°, in a yield of 91%.

EXAMPLE 2

23.4 g of 4-chloro-5-(2',4'-dichlorophenoxy)-1,2-phenylenediamine dihydrochloride are suspended in 60 ml of dioxane. A solution of 9 g of thiophosgene in 100 ml of dioxane is added dropwise to this suspension in the course of 20 minutes, with stirring. The temperature rises from 20° to 34° C. and a solution gradually forms. After 15 minutes, the solution is heated to 70°, stirred for a further 3 hours at this temperature and then evaporated to dryness. The residue is taken up in 300 ml of 2 N sodium hydroxide solution and the solution is twice extracted by shaking with, in each case, 200 ml of chloroform. The aqueous phase is acidified to pH 1 with concentrated hydrochloric acid and the precipitate which has formed is filtered off and washed with water until the wash water is neutral. The crude product is dissolved in hot dioxane, the solution is treated with active charcoal and filtered and the filtrate is diluted with hot water and cooled. After filtering off the product and drying in vacuo, this gives 18 g of 5-chloro-6-(2',4'-dichlorophenoxy)-2H-1,3-dihydro-benzimidazole-2-thione with a melting point of 309°–311° C., in a yield of 74%.

EXAMPLE 3

Preparation of
bis-[5-chloro-6-(2',4'-dichlorophenoxy)-2-benzimidazolyl]disulphide A suspension of 115 g of 5-chloro-6-(2',4'-dichlorophenoxy)-2H-1,3-dihydro-benzimidazole-2-thione and 50 g of anhydrous sodium acetate in 500 ml of absolute ethanol is cooled to 5° C. and, at this temperature, a solution of 46 g of iodine in 500 ml of absolute ethanol is added, with stirring. The mixture rapidly goes into solution and the solution is immediately concentrated in vacuo. The gel-like residue is dissolved in 1 l of chloroform and the insoluble constituent is filtered off. The filtrate is washed, first with an aqueous solution of sodium acetate and then several times with water, clarified with active charcoal, dried over magnesium sulphate and filtered and pentane is added at room temperature in the amount (about 300 ml) required to produce a slight turbidity. After cooling to 0° C., filtering off the precipitate and drying the latter at 60° C. in vacuo, this gives 79 g of light yellow bis-[5-chloro-6-(2',4'-dichlorophenoxy)-2-benzimidazolyl]disulphide with a melting point of 158°–160° C., which corresponds to a yield of 69%.

EXAMPLE 4

Preparation of
5-chloro-6-(2',4'-dichlorophenoxy)-1(3)-methoxycarbonyl-2H-1,3-dihydro-benzimidazole-2-thione 8 g of methyl chloroformate are added slowly dropwise to a solution, which has been cooled to 18° C., of 10.5 g of 5-chloro-6-(2',4'-dichlorophenoxy)-2H-1,3-dihydro-benzimidazole-2-thione in 100 ml of pyridine, with stirring and cooling. The mixture is stirred for a further 15 hours at room temperature and then poured into a mixture of 200 ml of concentrated hydrochloric acid and 350 g of ice and the precipitate is filtered off with suction. The material which has been filtered off with suction is washed with water until neutral, dried at room temperature and mixed to a suspension with 100 ml of absolute ethanol, the suspension is heated to the reflux temperature and then cooled to 5° C., water is added, the mixture is filtered and the product is dried in vacuo at 50° C. This gives 9.4 g of 5-chloro-6-(2',4'-dichlorophenoxy)-1(3)-methoxycarbonyl-2H-1,3-dihydro-benzimidazole-2-thione with a melting point of 167°–173° C., which corresponds to a yield of 77%.

The following compounds were prepared analogously to the examples above:

Table 1

| No. | $R_3$ | Z | Melting point in °C. |
|---|---|---|---|
| 1 | H | Cl–⟨phenyl⟩–O– | 268–270 |

Table 1-continued (structure: benzimidazole-2-thione with R3 and Z substituents)

| No. | R3 | Z | Melting point in °C |
|---|---|---|---|
| 2 | CH3 | 2,4-dichlorophenoxy | 290–293 |
| 3 | Cl | 2,4-dichlorophenoxy | 288–290 |
| 4 | Cl | 4-methoxyphenoxy | 267–268 |
| 5 | Cl | 2,4,6-trichlorophenoxy | 318–320 |
| 6 | Cl | phenoxy | 288–290 |
| 7 | Cl | 4-chlorophenoxy | 286–288 |
| 8 | Cl | 2-chloro-5-methylphenoxy | 283–285 |
| 9 | Cl | 2,4-dimethylphenoxy | 281–282 |
| 10 | Cl | 4-(methylthio)phenoxy | 268–270 |
| 11 | Cl | 3,5-dichlorophenoxy | 290–292 |
| 12 | Cl | 4-chloro-2-trifluoromethylphenoxy | 257–259 |
| 13 | Cl | 4-chloro-2-methylphenoxy | 306–308 |
| 14 | Cl | 4-cyanophenoxy | 296–298 |
| 15 | Cl | 3,5-dimethylphenoxy | 300–302 |
| 16 | Cl | 2,6-dichlorophenoxy | 335–337 |
| 17 | Cl | 2-chlorophenoxy | 300–303 |

Table 1-continued

| No. | R3 | Z | Melting point in °C |
|---|---|---|---|
| 18 | Cl | 2,3-dichlorophenoxy | 305–307 |
| 19 | Cl | 2-methylphenoxy | 301–303 |
| 20 | Cl | 4-bromo-2-chlorophenoxy | 325–327 |
| 21 | Cl | 2,4-dichlorophenoxy | 325–327 |
| 22 | Cl | 2,6-dimethylphenoxy | 288–290 |
| 23 | Cl | 2,4-dichlorophenylthio | 310–312 |
| 24 | Cl | phenylthio | 289–291 |
| 25 | Cl | 4-chlorophenylthio | 293–295 |
| 26 | H | 4-chlorophenylthio | 259–262 |
| 27 | H | 4-fluorophenylthio | 285–286 |
| 28 | H | phenylthio | 239–240 |
| 29 | H | 4-methylphenylthio | 283–284 |
| 30 | H | 4-methylphenoxy | 289–290 |
| 31 | H | phenoxy | 245–247 |
| 32 | Cl | 2-cyanophenoxy | 317–318 |
| 33 | CH3O— | 2,4-dichlorophenoxy | 308–311 |
| 34 | Cl | 2,6-dimethylphenoxy | 300–301 |

Table 1-continued

[Structure: benzimidazole-2-thione with R₃ and Z substituents]

| No. | R₃ | Z | Melting point in °C |
|---|---|---|---|
| 35 | Cl | 2,3-dimethyl-4-methoxyphenyl (H₃C, H₃C, —O—) | 288–289 |
| 36 | Cl | 3,5-dimethyl-2-methoxyphenyl (CH₃, H₃C, —O—) | 308–310 |
| 37 | Cl | 5-bromo-2-cyanophenyl (CN, Br) | 322–325 |
| 38 | Cl | 4-methoxyphenyl acetyl (CH₃—CO—, —O—) | 305–307 |
| 39 | Cl | 4-hydroxyphenoxy (HO—, —O—) | 305–308 |
| 40 | Cl | 2-methoxyphenoxy (OCH₃, —O—) | 275–276 |
| 41 | Cl | 4-(sec-butyl)phenoxy (H₃C—CH₂—CH(CH₃)—, —O—) | 300–301 |
| 42 | Cl | 4-chloro-2-methoxyphenoxy (OCH₃, Cl, —O—) | 286–288 |
| 43 | CH₃ | 4-chloro-2-methylphenoxy (CH₃, Cl, —O—) | 303–304 |
| 44 | CH₃ | 4-chloro-2-methoxyphenoxy (OCH₃, Cl, —O—) | 279–280 |
| 45 | CH₃ | 2,3-dichlorophenoxy (Cl, Cl, —O—) | 303–304 |
| 46 | CH₃ | 2,4-dichlorophenoxy (Cl, Cl, —O—) | 310–312 |
| 47 | CH₃ | 2,3-dimethylphenoxy (CH₃, CH₃, —O—) | 253–255 |
| 48 | CH₃ | 2-chlorophenoxy (Cl, —O—) | 310–312 |
| 49 | CH₃ | 2,5-dichlorophenylthio (Cl, Cl, —S—) | 331–332 |
| 50 | CH₃ | phenylthio (—S—) | 258–260 |

| No. | R₃ | Z | Melting point in °C |
|---|---|---|---|
| 51 | H | 2-methoxyphenoxy (OCH₃, —O—) | 232–235 |
| 52 | H | 2-chlorophenoxy (Cl, —O—) | 227–229 |
| 53 | H | 2,4-dichlorophenoxy (Cl, Cl, —O—) | 257–263 |
| 54 | H | 3,5-dichlorophenoxy (Cl, Cl, —O—) | 252–255 |
| 55 | H | 4-bromo-2-chlorophenoxy (Cl, Br, —O—) | 272–275 |
| 56 | H | 2,3,5-trichlorophenoxy (Cl, Cl, Cl, —O—) | 275–279 |
| 57 | H | 2-methylphenoxy (CH₃, —O—) | 236–240 |
| 58 | H | 4-chlorophenoxy (Cl—, —O—) | 265–270 |
| 59 | H | 3-methylphenoxy (CH₃, —O—) | 205–208 |
| 60 | H | 3,4-dichlorophenylthio (Cl, Cl, —S—) | 245–248 |
| 61 | H | 2,4-dichlorophenylthio (Cl, Cl, —S—) | 268–271 |
| 62 | Cl | 2-chloro-4-cyanophenoxy (Cl, NC—, —O—) | |
| 63 | CH₃ | 4-bromo-2-chlorophenoxy (Cl, Br, —O—) | |
| 64 | Cl | 4-nitrophenoxy (O₂N—, —O—) | |
| 65 | Cl | 2-chloro-4-nitrophenoxy (Cl, O₂N—, —O—) | |

Table 1-continued

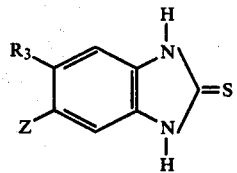

| No. | R₃ | Z | Melting point in °C. |
|---|---|---|---|
| 66 | H | NC–C₆H₄–O– | 260–270 |
| 67 | H | 2,3-Cl₂–C₆H₃–O– | 283–287 |
| 68 | H | 2,3-(CH₃)₂–C₆H₃–O– | |
| 69 | Cl | 2-Cl-3-CH₃–C₆H₃–O– | |
| 70 | CH₃ | CH₃SO₂–C₆H₄–O– | |
| 71 | Cl | CH₃SO₂–C₆H₄–O– (4-) | 304–306 |
| 72 | Cl | CH₃SO₂–(3-Cl)C₆H₃–O– | |
| 73 | Cl | CH₃O–(3-Cl)C₆H₃–O– | |
| 74 | Cl | CH₃–(3-Cl)C₆H₃–O– | |
| 75 | Cl | CH₃CO–(3-Cl)C₆H₃–O– | |
| 76 | Br | 2,4-Cl₂–C₆H₃–O– | |
| 77 | H | CH₃SO₂–C₆H₄–O– | 290 |
| 78 | Cl | 2-OH-5-Cl–C₆H₃–O– | 275–276 |
| 79 | H | 2,3-Cl₂–C₆H₃–O– | 294–298 |
| 80 | H | 2,3-(CH₃)₂–C₆H₃–O– | 267–275 |
| 81 | H | 2-C(CH₃)₃–C₆H₄–O– | 200–207 |
| 82 | CH₃O– | C₆H₅–O– | |

Table 1-continued

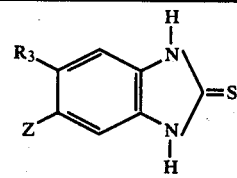

| No. | R₃ | Z | Melting point in °C. |
|---|---|---|---|
| 83 | CH₃O– | C₆H₅–S– | |
| 84 | C₂H₅O– | 2,3-Cl₂–C₆H₃–O– | |
| 85 | C₄H₉O– | 2,4-Cl₂–C₆H₃–O– | |

Table 2

| No. | Compound | Melting point in °C. |
|---|---|---|
| 1 | 4-Cl, 5-(2,4-Cl₂–C₆H₃–O–) benzimidazole-2-thione | 334–336 |
| 2 | 4,7-Cl₂, 5-(2,4-Cl₂–C₆H₃–O–) benzimidazole-2-thione | 350–355 |
| 3 | 4-Cl, 5-(4-Cl–C₆H₄–O–), with additional Cl, benzimidazole-2-thione | 291–294 |
| 4 | [5-Cl, 6-(2,4-Cl₂–C₆H₃–O–)-benzimidazol-2-yl-S–]₂ | 158–160 |

Table 3

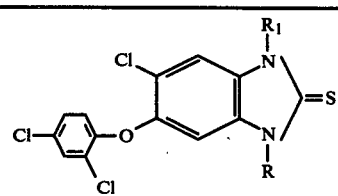

| No. | R | R₁ | Melting point in °C. |
|---|---|---|---|
| 1 | –COOC₂H₅* | H | 178–182 |

Table 3-continued

[Structure: benzimidazole derivative with R, R₁ substituents]

| No. | R | R₁ | Melting point in °C. |
|---|---|---|---|
| 2 | —COOCH₃* | H | 165–171 |
| 3 | —CO—⟨⟩—NO₂* | H | 158–160 |
| 4 | —COCH₃* | H | 230–232 |
| 5 | —COCH₃ | —COCH₃ | 144–145 |

*the structural formula

[Alternative structure shown]

is also possible.

The anthelmintic activity of the benzimidazole derivatives of the formula I is demonstrated with the aid of the following experiment:

Experiment on rats infested with *Fasciola hepatica*

White laboratory rats were infested with liver flukes (*Fasciola hepatica*). After the end of the pre-patency period, 3 infested rats per experiment were treated with the particular active ingredient, which was administered in the form of a suspension by probang, once per day on three successive days. Each active ingredient was tested in doses of 300, 100, 30 and 10 mg/kg of body weight. Two weeks after administration of the active ingredient, the test animals were killed and dissected.

An evaluation was made dissection of the test animals, by comparing the number of parasites which had remained in the bile ducts with that in untreated control animals infested in the same way and at the same time.

In therapeutically effective doses, the agent was tolerated by the rats without giving rise to symptoms.

Table 4

Minimal dose of active ingredient for full action against liver flukes

| Compound No. | Dose in mg/kg |
|---|---|
| Example 1 | 3×10 |
| 6 (T 1) | 3×300 |
| 13 (T 1) | 3×10 |
| 14 (T 1) | 3×100 |
| 17 (T 1) | 3×30 |
| 18 (T 1) | 3×10 |
| 19 (T 1) | 3×300 |
| 20 (T 1) | 3×10 |
| 21 (T 1) | 3×30 |
| 22 (T 1) | 3×30 |
| 28 (T 1) | 3×100 |
| 45 (T 1) | 3×10 |
| 46 (T 1) | 3×30 |
| 4 (T 2) | 3×30 |
| 1 (T 3) | 3×30 |
| 2 (T 3) | 3×300* |
| 5 (T 3) | 3×30 |

*not tested at a lower dose.

Toxicity values (acute)

Compound of Example 1:
 $LD_{50}$ rats, oral: 3,105 mg/kg
 $LD_{50}$ rats, dermal: >3,000 mg/kg
 $LD_{50}$ rabbits, oral: >6,000 mg/kg The active ingredients according to the invention are used for combating parasitic helminths in domestic and useful animals, such as cattle, sheep, goats, cats and dogs. They can be administered to the animals either as a single dose or repeatedly, the individual administrations being between 0.5 and 100 mg per kg of body weight, depending on the species of animal. By protracted administration, a better action is achieved in some cases, or it is possible to manage with lower total doses. The active ingredients, or the mixtures containing them, can also be added to the feed or the drinks. The ready-to-use feed contains the substances of the formula I preferably in a concentration of 0.005 to 0.1% by weight. The agents can be administered to the animals in the form of solutions, emulsions, suspensions (drenches), powders, tablets, bolusses or capsules, perorally or abomasally. Substances used to prepare these administration forms are, for example, conventional solid excipients, such as kaolin, talc, bentonite, sodium chloride, calcium phosphate and cottonseed meal, or liquids which do not react with the active ingredients, such as oils and other solvents and diluents harmless to the animal organism. If the physical and toxological properties of solutions or emulsions permit, the active ingredients can also be injected into the animals, for example subcutaneously. Furthermore, administration of the active ingredients to the animals by means of salt licks or molasses blocks is also possible.

If the anthelmintic agents are in the form of a feed concentrate, carrier substances used are, for example, hay, production rations, fodder grain or protein concentrates. Such feeds can also contain, in addition to the active ingredients, additives, vitamins, antibiotics, chemotherapeutic agents or other pesticides, mainly bacteriostatic agents, fungistatic agents and coccidiostatic agents or hormone preparations, substances having an anabolic action or other substances which promote growth, influence the quality of the meat of animals for slaughter or are useful to the organism in another way. They can also be combined with other anthelmintics, by which means their action is broadened and suited to given circumstances.

Other anthelmintics are:

Nematocides, for example Alcopar, ascariodole, Banminth II, bephenium, cambendazole, coumaphos, cyanin, diethylcarbamazine, DDVP, 1,4-di-(D-glyconyl)-piperazine, dithiazanine, Dow ET/57 Dowco 132, Gainex, hexachlorophene, hexylresorcinol, Jonit, levamisole, methylene violet, 1-methyl-1-tridecyl-piperazinium-4-carboxylic acid ethyl ester, methyridine, Neguvon, Nematodin, Nemural, Nidanthel, parbendazole, Parvex, phenothiazine, piperazine, polymethylenepiperazine, pyrantel, pyrvinium embonate, Rametin, ronnel, santonin, Shell 1808, stilbazium, tetramisole, thenium, thiabendazole, thymolane, Vermella, mebendazole, oxybendazole, fenbendazole, albendazole and oxfendazole; and Cestocides, for example Acranil, arecoline, Atebrin, bithionol, bithionol-sulphoxide, bunamidine, Cestondin, cambendazole, dibutyl-tin dilaurate, dichlorophene, dioctyl-tin dichloride, dioctyl-tin laurate, filixic acid, hexachlorophene, mepaesin, Nidanthel, praziquantel, Terenol and Yomesan.

The preparation of anthelmintic agents according to the invention is carried out in a manner known per se by intimate mixing and grinding of active ingredients of the general formula I with suitable excipients, if desired with the addition of dispersing agents or solvents which are inert towards the active ingredients.

The active ingredients can be present, and can be employed, in the following processing forms:

Solid processing forms:
  granules, coated granules, impregnated granules and homogeneous granules.
  Active ingredient concentrates dispersible in water (wettable powders).

Liquid processing forms:
  solutions, pastes, emulsions and especially ready-to-use suspensions (drenches).

The particle size of the excipients is advantageously up to about 0.1 mm for dusting agents and wettable powders and 0.01-0.5 mm for granules.

The concentrations of active ingredient are 0.5 to 80% in the solid processing forms and 0.5 to 50% in the liquid processing forms.

Additives which stabilise the active ingredient and/or non-ionic, anionic and cationic substances, which, for example, ensure better wettability (wetting agents) and dispersibility (dispersing agents), can also be added to these mixtures.

EXAMPLE

Powder mixture dispersible in water 25 parts by weight of an active ingredient of the formula (I) are mixed intensively, in a mixing appartus, with 7.5 parts by weight of an absorbent excipient, for example silica, and 59.4 parts by weight of an excipient, for example Bolus alba or kaolin, and 0.5 part by weight of oleic acid and 5.3 parts by weight of octylphenyl polyglycol ether and 2.3 parts by weight of a stearylbenzimidazole derivative.

This mixture is ground down to a particle size of 5-15 μm in a pin mill or air jet mill. The wettable powder obtained in this way gives a good suspension in water.

What is claimed is:

1. A method for combating parasitic helminths in animals which comprises administering to an animal infested with said helminths an anthelmintically effective amount of a compound of the formula

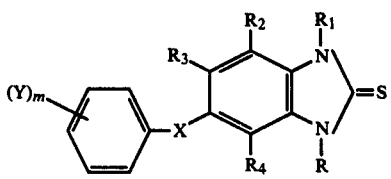

in which
  each of R and $R_1$ is hydogen, alkanoyl of from 1 to 4 carbon atoms, alkoxycarbonyl or from 1 to 4 carbon atoms, alkylsulphonyl of from 1 to 4 carbon atoms, benzoyl, phenylsulphonyl or p-methylphenylsulphonyl,
  each of $R_2$ and $R_4$ is hydrogen, halogen or methyl,
  $R_3$ is hydrogen, halogen, methyl or methoxy,
  X is oxygen or sulphur,
  Y is halogen, alkyl of from 1 to 4 carbon atoms, alkoxy of from 1 to 4 carbon atoms, methylthio, methylsulphinyl, methylsulphonyl, trifluoromethyl, nitro, hydroxyl, cyano or acetyl, and
  m is 0, 1, 2 or 3, including the possible tautomers of said compound and the disulphide of the formula

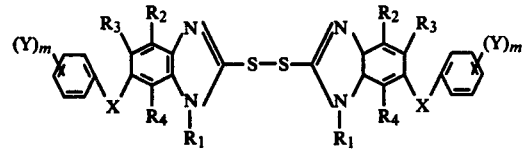

obtainable by oxidation of said compound in which R is hydrogen.

2. A method according to claim 1 in which, in the compound,
  each of R and $R_1$ is hydrogen, alkanoyl of from 1 to 4 carbon atoms, alkoxycarbonyl of from 1 to 4 carbon atoms, or benzoyl,
  $R_2$ and $R_4$ are hydrogen,
  $R_3$ is hydrogen, chlorine or methyl, and
  Y is halogen, methyl, methoxy, methylthio, methylsulphinyl, methylsulphonyl, nitro, hydroxyl, cyano or acetyl.

3. A method according to claim 2 in which, in the compound.
  R and $R_1$ are hydrogen,
  Y is halogen, methyl, methoxy, methylthio, methylsulphinyl, cyano or acetyl, and
  m is 0, 1 or 2.

4. A method according to claim 3 in which, in the compound,
  x is oxygen,
  Y is halogen or methyl with the 2-position being substituted in the 6-position being unsubstituted, and
  m is 1 or 2.

5. A method according to claim 1 in which the helminths are trematodes.

6. A method according to claim 5 in which the helminths are *Fasciola hepatica*.

7. A method according to claim 4 in which the compound is 5-chloro-6-(2',4'-dichlorophenoxy)-2H-1,3-dihydrobenzimidazole-2-thione.

8. A method according to claim 4 in which the compound is 5-chloro-6-(2',3'-dichlorophenoxy)-2H-1,3-dihydrobenzimidazole-2-thione.

* * * * *